(12) United States Patent
Pechstein

(10) Patent No.: US 6,624,637 B1
(45) Date of Patent: Sep. 23, 2003

(54) DEVICE FOR MEASURING THE CONCENTRATIONS IN A MEASURING LIQUID

(75) Inventor: Torsten Pechstein, Waldheim (DE)

(73) Assignee: Endress + Hauser Conducta Gesellschaft für Mess - und Regeltechnik mbH + Co. (DE)

(*) Notice: Subject to any disclaimer, the term of this patent is extended or adjusted under 35 U.S.C. 154(b) by 0 days.

(21) Appl. No.: 09/856,511
(22) PCT Filed: Dec. 11, 1999
(86) PCT No.: PCT/EP99/09804
§ 371 (c)(1), (2), (4) Date: Sep. 13, 2001
(87) PCT Pub. No.: WO00/36408
PCT Pub. Date: Jun. 22, 2000

(30) Foreign Application Priority Data

Dec. 16, 1998 (DE) .......................................... 198 57 953

(51) Int. Cl.⁷ .................. G01N 27/416; G01N 27/00
(52) U.S. Cl. ...................... 324/438; 324/71.6; 324/71.2
(58) Field of Search .................... 324/438, 71.6, 324/71.2; 204/413, 418, 406, 416, 401; 257/253, 252; 435/7.4

(56) References Cited

U.S. PATENT DOCUMENTS

| | | | | |
|---|---|---|---|---|
| 3,706,649 A | * | 12/1972 | Cosgrove et al. ............ 204/418 |
| 4,020,830 A | * | 5/1977 | Johnson et al. ............. 600/348 |
| 4,066,092 A | * | 1/1978 | Dulger et al. ................. 137/93 |
| 4,269,682 A | * | 5/1981 | Yano et al. .................. 204/418 |
| 4,298,971 A | * | 11/1981 | Morokawa et al. ......... 368/204 |
| 4,332,658 A | * | 6/1982 | Tsubshima ............. 204/195 M |
| 4,334,880 A | * | 6/1982 | Malmros ..................... 435/7.4 |
| 4,352,726 A | * | 10/1982 | Sugano et al. .............. 204/413 |
| 4,411,741 A | * | 10/1983 | Janata ......................... 257/253 |
| 4,444,644 A | * | 4/1984 | Hiramoto et al. ........... 204/406 |
| 4,488,556 A | * | 12/1984 | Ho .............................. 128/635 |
| 4,592,824 A | * | 6/1986 | Smith et al. ................. 257/253 |
| 4,701,253 A | * | 10/1987 | Ligtenberg et al. ......... 204/416 |
| 4,776,944 A | * | 10/1988 | Janata et al. ................ 204/403 |
| 4,921,591 A | * | 5/1990 | Mochizuki et al. ......... 204/412 |
| 4,963,815 A | * | 10/1990 | Hafeman ................. 205/777.5 |
| 5,039,390 A | * | 8/1991 | Hampp et al. .............. 204/412 |
| 5,078,855 A | * | 1/1992 | Mochizuki et al. ......... 204/418 |
| 5,087,899 A | * | 2/1992 | Lauper ...................... 333/81 R |
| 5,152,758 A | * | 10/1992 | Kaetsu et al. ............. 604/890.1 |
| 5,240,586 A | * | 8/1993 | Moore et al. ............... 204/418 |
| 5,583,462 A | * | 12/1996 | Graaahoff ................... 327/262 |
| 5,911,873 A | * | 6/1999 | McCarron et al. .......... 205/789 |
| 6,008,685 A | * | 12/1999 | Kunst ......................... 327/512 |
| 6,205,010 B1 | * | 3/2001 | Ohsaka et al. .............. 361/103 |
| 6,259,333 B1 | * | 7/2001 | Shimono ................ 331/116 R |

FOREIGN PATENT DOCUMENTS

| | | |
|---|---|---|
| EP | 0 155 725 A1 | 9/1985 |
| EP | 0 315 790 A1 | 5/1989 |
| EP | 0 751 392 A2 | 1/1997 |

OTHER PUBLICATIONS

Analytical and Biomedical Applications of Ion–Selective Field Effect Transistors, P. Bergveld, A. Sibbald, Elsevier Science Publishers B.V. Amsterdam 1988, Chapter 8, ISFET instrumentation, pp. 101–112.

* cited by examiner

*Primary Examiner*—Andrew H. Hirshfeld
*Assistant Examiner*—Wasseem H. Hamdan
(74) *Attorney, Agent, or Firm*—Hoffman, Wasson & Gitler

(57) ABSTRACT

The invention relates to a device for measuring the concentration of ions, notably of hydrogen ions, in a measuring liquid using at least one ion-sensitive field effect transistor which is integrated into an electric circuit within the device in such a way that said circuit emits an output signal which serves as measure of the ion concentration in the measuring liquid. To provide a circuit which is as simple as possible and in particular comprises as few components as possible, the invention provides for the at least one pH-ISFET to be bridge-connected with at least three resistors.

12 Claims, 3 Drawing Sheets

DEVICE FOR MEASURING THE CONCENTRATIONS IN A MEASURING LIQUID

BACKGROUND OF THE INVENTION

This invention relates to a device for measuring the concentration of ions, especially H⁺ ions, in a measurement liquid. Measurement takes place by means of at least one ion sensitive field effect transistor (ISFET) which is located in the measurement liquid and which is connected together with the resistors in a bridge circuit. There is a bridge feed voltage at the feed points of the bridge circuit. The device delivers an output signal which is a measure of the ion concentration in the measurement liquid. The device has a reference electrode which is likewise located in the measurement liquid.

These devices are conventionally used to measure the pH of a measurement liquid. The pH is determined by the host of constituents dissolved in the measurement liquid, for example, by the concentration of H⁺ or OH⁻ ions.

In community and industrial waste water treatment, chemical reactions are used to precipitate certain constituents, to neutralize and detoxify the water. The pH plays a key role for the correct progression of these reactions. The mechanical settling processes in the clarification plants can be adversely affected by acid or alkali waste water. Biological processes in self-purification of water or in the aerobic and anaerobic biological stages of clarification plants are likewise linked to certain pH values and their progression is disrupted when there are deviations therefrom. To automate these operations continuous measurement of the pH is essential.

The concentration of H⁺ ions in a measurement liquid can be measured for example by means of an ion-sensitive field effect transistor (pH-ISFET), especially by means of a hydrogen ISFET. Compared to conventional glass electrode measurement chains, pH ISFETS have the advantage that they are not sensitive to aging and therefore have a much longer service life. The resistance of the channel of the pH-ISFET and thus the gate potential change linearly with respect to the concentration of H⁺ ions in the measurement liquid. So that the pH-ISFET delivers an output signal which is proportional to the input voltage on the pH-ISFET, there is a constant drain current on the pH-ISFET. The pH-ISFET delivers an output voltage as the output signal, for example. This output voltage is measured against a reference electrode which cannot be influenced by the concentration of H⁺ ions and which is likewise located in the measurement liquid.

EP 0 155 725 discloses a device of the initially mentioned type in which a pH-ISFET and a reference ISFET are connected together with two resistors in a bridge circuit. U.S. Pat. No. 4,334,880 discloses another device of the initially mentioned type, but without a reference electrode. The circuit described in the patent includes a pH-ISFET with three resistors being connected in a bridge circuit. The diagonal voltage of the bridge circuit is used as the output signal of the device. The conductivity of the pH-ISFET changes during the measurement process depending on the ion concentration in the measurement liquid, by which the measurement bridge is detuned and a diagonal voltage is formed.

Devices known in the prior art differ among one another especially in how the pH-ISFET is integrated into the circuitry of the device. In *Analytical and Biomedical Applications of Ion-Selective Field Effect Transistors*, P. Bergveld, A. Sibbald, Elsevier Science Publishers B.V. Amsterdam 1988, Chapter 8, ISFET instrumentation, pp. 101–107, different types of interconnection of a pH-ISFET in a device of the initially mentioned type are disclosed. FIG. 8.3 illustrates a circuit diagram which is detailed in section 8.5. Accordingly the pH-ISFET is integrated into an electrometer subtractor (with operational amplifiers $A_1$, $A_2$, $A_3$) such that it is located in the circuit at the site of that resistor of the electrometer subtractor by which the gain of the electrometer subtractor can be adjusted. The electrometer subtractor has a power supply with a current source which delivers a constant current I and an adjustable reference voltage $V_{ref}$. At the input of the electrometer subtractor on a resistor $R_1$ there is a constant voltage I×$R_1$. The output signal of the electrometer subtractor delivers an output voltage which is inversely proportional to the resistance of the channel of the pH-ISFET. The output voltage is inverted by means of an inverter ($A_4$). Finally, the difference between the inverted output voltage and the reference voltage $V_{ref}$ is amplified by means of an operational amplifier ($A_5$). The output of the final operational amplifier ($A_5$) is fed back to the input of the electrometer subtractor so that a feedback current flows via the resistor ($R_2$). In this way the source and drain voltages of the pH-ISFET can be controlled. Based on this control the drain current ($I_D$) and the drain source voltage ($V_{DS}$) can be kept constant.

The connection of the pH-ISFET in an electrometer subtractor however has the disadvantage that this circuit is very complex to build. In particular, it requires a large number of components, for example three operational amplifiers ($A_1$, $A_2$, $A_3$) and six ohmic resistances ($R_3$, $R_4$, $R_5$, $R_6$, $R_7$, $R_8$). Due to the large number of components the production of the circuit is time-consuming and complex. The known connection of the pH-ISFET is moreover extremely susceptible to temperature drift.

SUMMARY OF THE INVENTION

The object of this invention is therefore to embody and develop a device of the initially mentioned type such that a pH-ISFET is integrated in a circuit which is as simple as possible, which has a limited number of components, and which at the same time is not very susceptible to temperature drift and has high measurement accuracy.

To achieve this object the present invention proposes that at least one pH-ISFET with at least three resistors be connected in a bridge circuit, the diagonal voltage of the bridge circuit is between the p-input and the n-input of an operational amplifier, with an output which is fed back via two resistors of the bridge circuit to the inputs of the operational amplifier and the output signal of the device is formed as an output voltage which is formed from the difference of the drain potential of the pH-ISFET and the reference potential of the reference electrode.

In this way the pH-ISFET is integrated in a circuit of especially simple structure. The circuit consists of an extremely small number of components and can thus be produced economically. In spite of the simple structure of the circuit, the device of the present invention has all the features necessary to ensure proper operation of the pH-ISFET. Thus, the pH-ISFET operated in the circuit delivers, for example, an output signal which is proportional to the input voltage on the pH-ISFET. Moreover, the output signal is a reliable measure of the ion concentration in the measurement liquid and thus of the pH of the measurement liquid. There is preferably a linear relationship between the common logarithm of the H⁺ ion concentration in the measurement liquid and the output signal of the device.

The drain source voltage $U_{DS}$ on the pH-ISFET is set using the bridge feed voltage $U_{BSS}$ and the resistors $R_2$ and $R_3$ via which the output of the first operational amplifier is fed back to the inputs of the first operational amplifier. Here the following relationship applies:

$$U_{DS}=U_{BSS}\times[R_3/(R_2+R_3)]$$

The drain source current $I_{DS}$ can then be set by means of the drain source voltage $U_{DS}$ and of the resistor $R_1$ via which the output of the first operational amplifier is fed back to the inputs of the first operational amplifier. Here the following relationship applies:

$$I_{DS}=(U_{BSS}-U_{DS})/R_1$$

By means of these relationships the working point of the pH-ISFET can be easily set without changing the bridge feed voltage $U_{BSS}$.

The drain potential linearly follows the change of the gate potential caused by the change of the pH, since the operational amplifier works as a P controller. The control circuit has the following transfer function:

$$\partial\phi_D/\partial\phi_G=1.$$

In the adjusted state of the circuit, the bridge is balanced, i.e. the diagonal voltage $U_d=0$. In the balanced state of the bridge, between the two series-connected resistors on one side of the bridge there is the same potential as between the resistor and the drain of the pH-ISFET on the other side of the bridge. Therefore, in the balanced state of the bridge, the output signal can also be tapped between the two series-connected resistors on one side of the bridge.

Each of the three resistors of the bridge circuit can of course also be replaced by a host of series-connected or parallel-connected resistors. The output signal can be tapped anywhere between these resistors. Depending on the size of the individual resistors, the output signal which has been tapped in this way is shifted by an offset voltage compared to the output signal tapped originally between the two series-connected resistors on one side of the bridge circuit or between the drain of the pH-ISFET and the resistor on the other side of the bridge circuit. In this way the zero point of the circuit (generally at pH 7) can be set independently of the other operating quantities of the pH-ISFET (especially the drain source voltage $U_{DS}$ and the drain source current $I_{DS}$).

The output signal of the device is independent of temperature influences, since the device has a reference electrode which is likewise located in the measurement liquid. The output signal is formed as the output voltage which is formed from the difference of the drain potential of the pH-ISFET and the reference potential of the reference electrode.

According to one preferred development of the present invention, it is proposed that the device have a reference ISFET which is likewise located in the measurement liquid, the output signal being formed as an output voltage which is formed from the difference of the drain potential of the pH-ISFET and the drain potential of the reference ISFET. The reference ISFET is advantageously connected in a bridge circuit like the pH-ISFET of the device. According to this development, the conventional glass electrode for measuring the ion concentration is replaced by a pH-ISFET. Rather the reference electrode made as a conventional glass electrode is also replaced by an ISFET.

Advantageously the output of the first operational amplifier is routed back via a capacitor to the n-input of the first operational amplifier. In this way vibrations of the device can be suppressed.

According to one preferred embodiment of this invention the resistors are made as ohmic resistances. But it is also conceivable to replace the resistors via which the output of the operational amplifier is fed back to the inputs of the first operational amplifier by current sources. A current source can be built using a field effect transistor operated at saturation.

So that the device delivers an output signal which has light sensitivity as low as possible, according to one advantageous development of the invention it is proposed that the drain potential of the pH-ISFET and the pseudoreference potential of a potential reference electrode form a first difference signal, and the drain potential of the reference ISFET and the pseudoreference potential form a second difference signal, the output signal being formed as the difference of the first and the second difference signal, and the same light conditions prevailing on the gate regions of the pH-ISFET and the reference ISFET. The potential reference electrode is preferably made as a metal pin which is provided with a silver or a silver chloride coating. The reference ISFET is located in a measurement chamber with a constant pH (for example, pH=7). The measurement chamber is connected to the measurement liquid via a diaphragm.

In this device the pH-ISFET and the reference ISFET are operated in the so-called difference mode against the pseudoreference potential of the potential reference electrode. As a result of the difference formation the light-dependent signal portions of the pH-ISFET and of the reference ISFET, the two difference signals are almost completely compensated. Thus the output signal is also for the most part independent, under identical light conditions of the gate regions of the pH-ISFET. The reference ISFET is completely independent of the light conditions.

In this device, which is operated in the difference mode against the pseudoreference potential of the potential reference electrode, the pH ISFET together with at least three resistors is advantageously connected in a bridge circuit.

The bridge feed voltage is preferably constant. The constant bridge feed voltage is used by the operational amplifier of the circuit of the device of the present invention to produce an output voltage as stable as possible. The stability of the output voltage cannot be better than that of the bridge feed voltage. To keep the bridge feed voltage as stable as possible, it is important that the voltage source be as stable as possible.

There are various possibilities known for producing a constant voltage. According to one preferred embodiment it is proposed that the bridge feed voltage be formed as the energy gap voltage of a so-called bandgap diode.

Preferably the drain source voltage of the pH-ISFET is constant during the measurement process. In addition, or alternatively, the drain source current of the pH-ISFET is constant during the measurement process. The operating state in which both the drain source voltage and also the drain source current are constant is also called the constant charge mode (CCM). The gate of the ISFET represents a capacitor. By operating the ISFET in CCM, the capacitor charge remains constant, by which no recharging processes occur. In this way the ISFET can respond more quickly and it delivers a more accurate measured value since the hysteresis effect cannot occur.

DETAILED DESCRIPTION OF THE PREFERRED EMBODIMENTS

Figure 1:
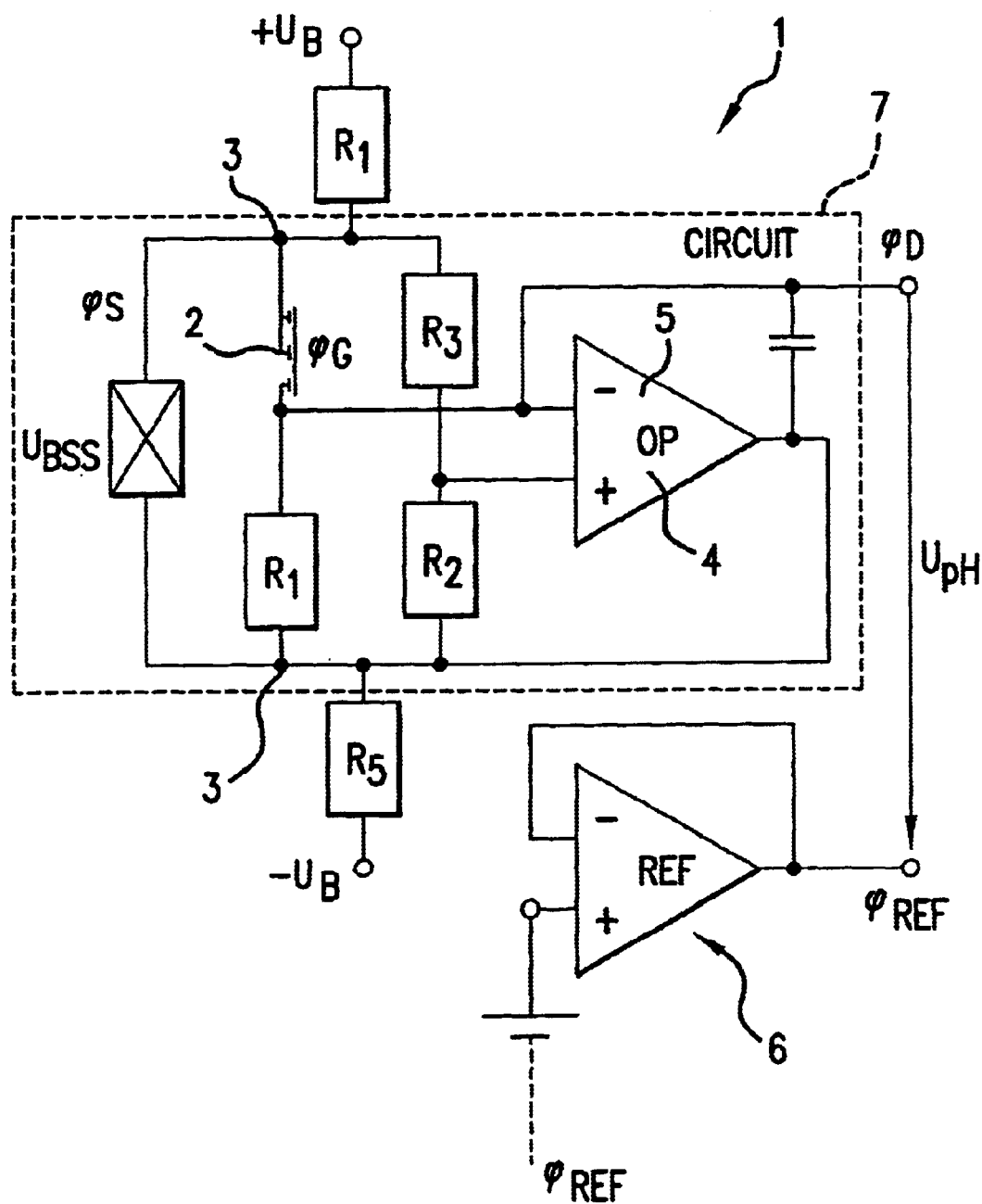
FIG. 1 shows a circuit diagram of the device of the present invention according to a first embodiment.

In FIG. 1 a device as claimed in the invention is labeled in its entirety with reference number 1. The device 1 has an electronic circuit in which an ion-sensitive field effect transistor (pH-ISFET) 2, is integrated. By means of the pH-ISFET 2, the concentration of ions in the measurement liquid can be measured. Consequently, the pH of the measurement liquid can be determined from the ion concentration.

The pH-ISFET 2 together with the three resistors ($R_1$, $R_2$, $R_3$) is connected in a bridge circuit. Via two feed points 3, there is a constant bridge feed voltage $U_{BSS}$ on the bridge circuit. The diagonal voltage $U_D$ of the bridge circuit is between the p-input 4 and the n-input 5 of a first operational amplifier OP. The output of the operational amplifier OP is fed back via two of the three resistors ($R_1$, $R_2$) of the bridge circuit to the inputs 4, 5 of the operational amplifier OP. On the n-input 5 of the operational amplifier OP is the drain potential $\phi_D$ of the pH-ISFET 2. The operational amplifier OP works as a P controller in the circuit. For this reason the drain potential $\phi_D$ follows the gate potential $\phi_G$. The first operational amplifier OP is interconnected symmetrically, i.e. at its inputs 4, 5 there is roughly the same impedance with respect to the ground. This has the advantage that common mode noise at the inputs 4, 5 can be better compensated as a result of temperature-induced resistance changes. This leads to better linearity of the operational amplifier OP.

Changing the pH of the measurement liquid changes the gate potential $\phi_G$ of the pH-ISFET 2. This leads to a change of the channel resistance and thus also to a change of the drain potential $\phi_D$. The n-input 5 of the operational amplifier OP with the drain potential $\phi_D$ is routed out of the device 1. The difference between the drain potential $\phi_D$ and the reference potential $\phi_{REF}$ is called the output voltage $U_{pH}$. The output voltage $U_{pH}$ is the output signal of the device 1 and is proportional to the pH of the measurement liquid. The output voltage $U_{pH}$ of the circuit is largely independent of the temperature as a result of the symmetrical structure of the circuit. In the device 1 shown in FIG. 1 the reference potential $\phi_{REF}$ is produced by a reference electrode 6 which is likewise located in the measurement liquid. It is also conceivable for the reference electrode 6 to be replaced by another device of the present invention (compare FIG. 2). The drain potential of the other device as recited in the present invention could be used as a reference potential $\phi_{REF}$.

The resistors $R_4$, $R_5$ and the remaining circuit 7 of the device 1 act as voltage dividers. Between the feed points 3 a voltage which is different from the operating voltage $+U_B$, $-U_B$ (bridge feed voltage $U_{BSS}$) can be adjusted. The bridge feed voltage $U_{BSS}$ is formed as a so-called floating voltage reference without a fixed reference potential. At the top feed point 3 of the remaining circuit 7 a potential between $+U_B-U_{R4}$ and $-U_B+U_{BSS}+U_{R5}$ can be set. At the bottom feed point 3 of the remaining circuit 7 a potential between $+U_B-U_{BSS}-U_{R4}$ and $-U_B+U_{R4}$ can be set. Between the two feed points 3 however there is always the bridge feed voltage $U_{BSS}$.

Figure 2:
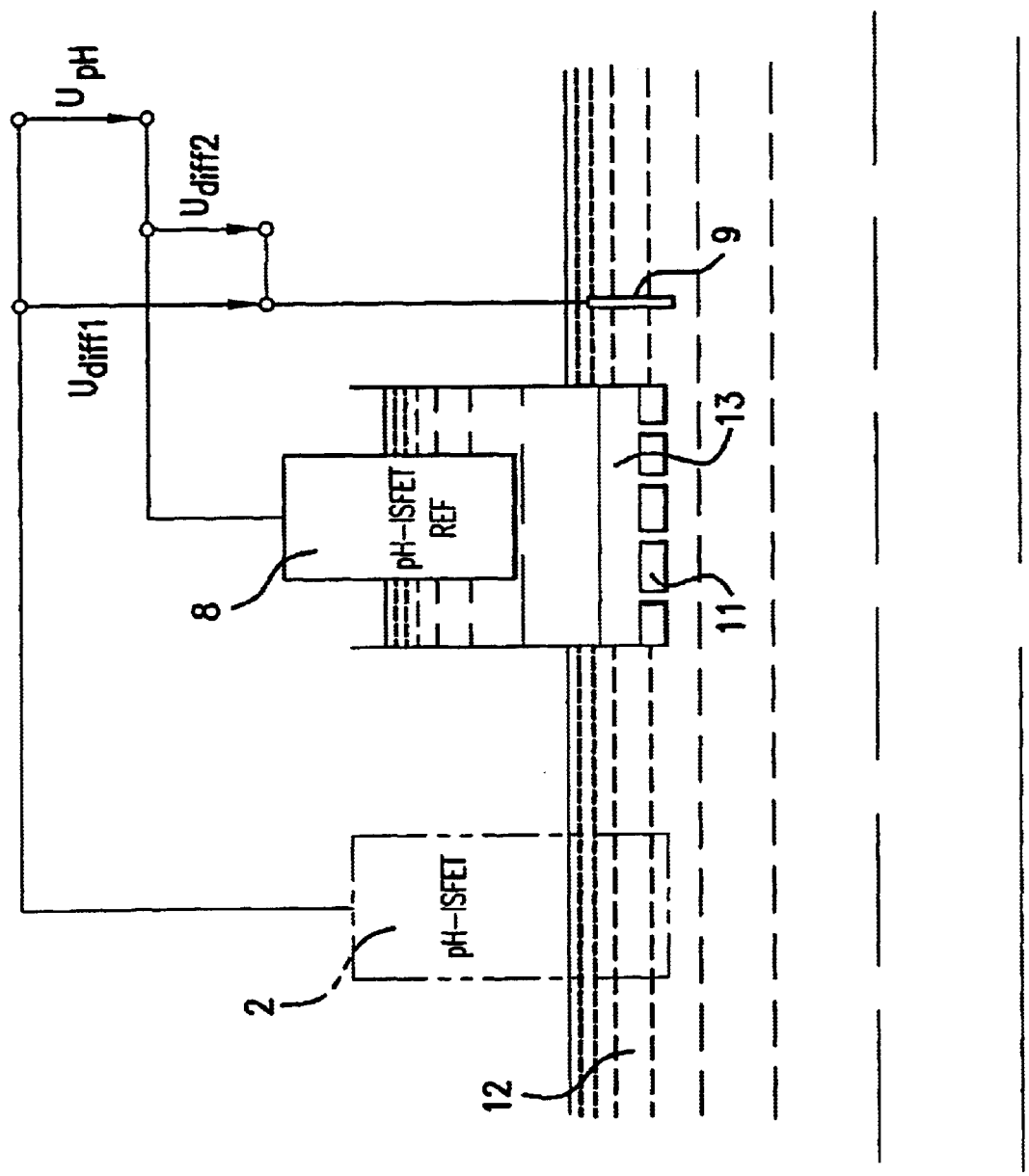
FIG. 2 shows a schematic of a device of the present invention according to a second embodiment.

FIG. 2 shows a device 1 of the present invention, in which the reference electrode 6 is made as a reference ISFET 8. So that the device 1 from FIG. 2 delivers an output signal $U_{pH}$, which has light sensitivity as low as possible, the drain potential $\phi_D$ of the pH-ISFET 2 and the pseudoreference potential of a potential reference electrode 9 form a first difference signal $U_{diff1}$, and the drain potential $\phi_{REF}$ of the reference ISFET 8 and the pseudoreference potential form a second difference signal $U_{diff2}$. The output signal $U_{pH}$ is formed as the difference of the first difference signal $U_{diff1}$ and the second difference signal $U_{diff2}$. On the gate regions of the pH-ISFET 2 and the reference ISFET 8 preferably the same light conditions prevail. The potential reference electrode 9 is made preferably as a metal pin which is provided with a silver or silver chloride coating. The reference ISFET 8 is located in a measurement chamber 10 in which a reference solution 13 with a constant pH (for example, pH=7) is located. The measurement chamber 10 is connected via a diaphragm 11 to the measurement liquid 12.

Figure 3:
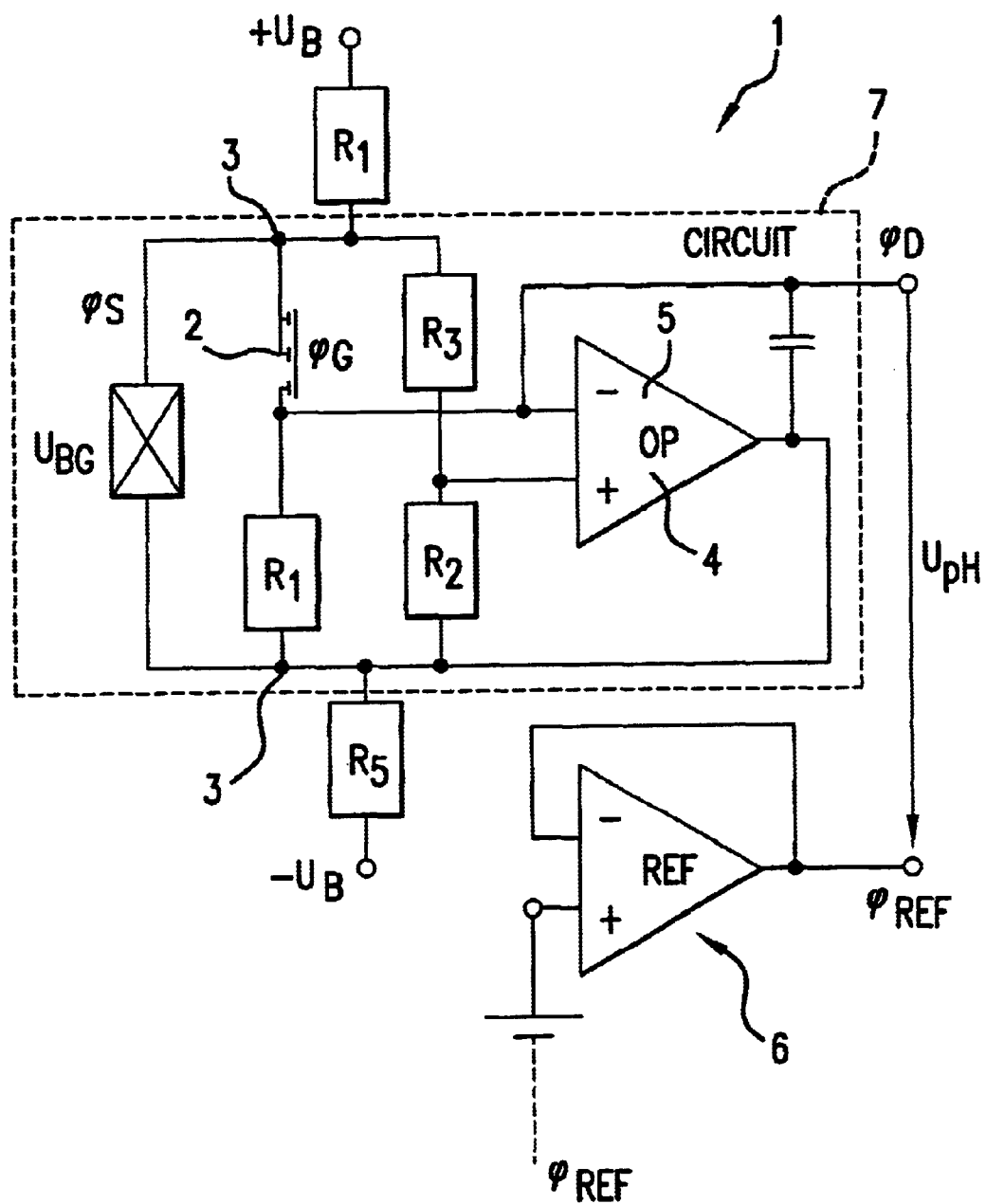
FIG. 3 shows a schematic of the device of the present invention according to a third embodiment.

FIG. 3 illustrates a device very similar to the device shown in FIG. 1 with the same elements keeping the same reference numerals. The only difference between the device illustrated in FIG. 1 and the device illustrated in FIG. 3 is that the bridge feed voltage $U_{BSS}$ shown in FIG. 1 has been substituted by the band gap potential $U_{BG}$ illustrated in FIG. 3.

What is claimed is:

1. A device for measuring the concentration of ions in a measurement liquid, comprising:

at least one ion sensitive field effect transistor (pH-ISFET) having a drain provided in the measurement liquid;

a bridge circuit having at least three resistors, said bridge circuit provided with feed points having a feed voltage and a diagonal voltage, said bridge circuit connected to said pH-ISFET;

an operational amplifier having a p-input and an n-input, said operational amplifier connected to said bridge circuit, said diagonal voltage of said bridge circuit being between said p-input and said n-input of said operational amplifier, said n-input connected to said drain, the output of said operational amplifier being fed back to said bridge circuit; and a reference electrode provided in the measurement liquid;

wherein an output signal is produced by the device which measures the ion concentration of the measurement liquid, said output signal formed as the output voltage from the difference of the drain potential of said pH-ISFET on said n-input and the reference potential of said reference electrode.

2. The device in accordance with claim 1, wherein said reference electrode is an ion sensitive field effect transistor (ISFET).

3. The device in accordance with claim 2, wherein said reference electrode is provided in a reference liquid.

4. The device in accordance with claim 3, wherein said reference liquid has a pH of 7.

5. The device in accordance with claim 3, further including a potential reference electrode provided in the measurement liquid, wherein the drain potential of said pH-ISFET and a pseudoreference potential of said potential reference electrode form a first difference signal and the drain potential of said ISFET and the pseudoreference potential of said potential reference electrode form a second difference signal said output signal being formed as the difference of said first difference signal and said second difference signal, with the same light conditions prevailing on the gate region of said pH-ISFET and said reference ISFET.

6. The device in accordance with claim 1, wherein the output of said operational amplifier is routed back via a capacitor to said n-input of said operational amplifier.

7. The device in accordance with claim 1, wherein said bridge circuit includes resistors made as ohmic resistance.

8. The device in accordance with claim 1, wherein said reference electrode is provided within the measurement liquid.

9. The device in accordance with claim 1, wherein said bridge feed voltage is formed as the energy gap voltage of a bandgap diode.

10. The device in accordance with claim 1, wherein the drain source voltage said pH-ISFET is constant.

11. The device in accordance with claim 1, wherein the drain source current of said pH-ISFET is constant.

12. The device in accordance with claim 1, wherein said device is used to measure hydrogen ($H^+$) ions.

* * * * *